United States Patent [19]
Bedford

[11] Patent Number: 4,866,806
[45] Date of Patent: Sep. 19, 1989

[54] SURGICAL SCRUB SPONGE

[76] Inventor: Peter H. Bedford, 3817 Mistral Ave., Huntington Beach, Calif. 92649

[21] Appl. No.: 198,281

[22] Filed: May 25, 1988

[51] Int. Cl.⁴ .............................................. B08B 1/00
[52] U.S. Cl. ................. 15/104.94; 15/167.3; 15/118; 15/244.4
[58] Field of Search ...................... 15/167.3, 105, 118, 15/104.93, 104.94, 244.1, 244.2, 244.3, 244.4; 132/321, 329; 206/361

[56] References Cited

U.S. PATENT DOCUMENTS

| | | |
|---|---|---|
| 2,841,811 | 7/1958 | Carroll ............................... 15/244.1 |
| 3,354,492 | 11/1967 | Baumgartner . |
| 3,570,036 | 3/1971 | Gilchrist et al. ................... 15/244.1 |
| 3,611,468 | 10/1971 | Michael ............................ 15/118 X |
| 3,694,845 | 10/1972 | Engelsher .......................... 15/244.4 |
| 3,924,286 | 12/1975 | Miller . |
| 3,966,335 | 6/1976 | Abramson . |
| 4,420,853 | 12/1983 | Gilman et al. . |
| 4,479,277 | 10/1984 | Gilman et al. . |
| 4,530,726 | 7/1985 | Montiel . |

Primary Examiner—Peter Feldman
Attorney, Agent, or Firm—Price, Gess & Ubell

[57] ABSTRACT

A multilayered foam scrub sponge for cleanup prior to a surgical procedure is described. One layer serves to impart a degree of rigidity to the structure, another layer retains an antiseptic solution, while a third layer acts as a scrubbing surface. The sponge is shaped to fall easily to the human hand. A toothed profile on the edges presents a rough surface for an augmented scrubbing capability. A removable serrated insert accommodated in the center of the sponge enables insertion of the fingers to cleanse and disinfect the cuticle areas. Removal of the insert allows access to a fingernail pick stored thereunder. The sponge is stored in a solution-impregnated state within a sealed package ready for immediate use.

20 Claims, 1 Drawing Sheet

SURGICAL SCRUB SPONGE

BACKGROUND OF THE INVENTION

1. Field of the Invention

The present invention relates to scrub sponges, and in particular relates to a sponge especially suited for cleaning arms, hands, fingernails and cuticles prior to a surgical procedure.

2. Description of the Prior Art

Prior to a surgical procedure in an operating room, it is essential that the surgeon and the assistants thoroughly clean and disinfect their hands and arms. Particular attention must be paid to the areas under the fingernails and around the cuticles, as they are especially prone to trapping infective agents. It is most desirable that this can be performed in the simplest and most expeditious manner. An assortment of scrub brushes is normally available to be utilized in this mandatory scrubbing procedure. Brushes having long and relatively soft bristles are intended for cleaning the large exposed surfaces of the arms and hands, while brushes having relatively short and stiff bristles are used for cleaning in and around the cuticles and under the fingernails. In order to further simplify and expedite this procedure, devices have been described that combine in a single brush, long and soft as well as short and stiff bristles, see, for instance, Baumgartner, U.S. Pat. No. 3,354,492. Complex geometric configurations of bristles of various lengths are disclosed in Abramson, U.S. Pat. No. 3,966,335, to allow the simultaneous cleansing of four fingers. Gilman et al., U.S. Pat. Nos. 4,420,853 and 4,479,277, discloses a device in which a bristle surface is combined with a sponge, in addition to providing a pointed implement for cleaning under the fingernails. A cleansing solution and/or an anti-microbial solution can be absorbed in the sponge, to facilitate an efficient cleansing and disinfecting of the hands.

All of the described devices which employ an array of bristles require a reasonably rigid base to prevent substantial deformation of the scrub brush during use. Although useful insofar as providing the required support to the bristles, this property does have the disadvantage of limiting the device to rather superficial movements, as maneuvering in between the fingers, for example, would require a substantial deformation of the brush as a whole.

A further disadvantage, especially in the more specialized devices, is their rather complex and therefore relatively expensive structure requiring the use of a number of different types of materials and their intricate assembly. As the use of all such devices in a surgical environment precludes their reuse, it is most desirable that they be relatively inexpensive and therefore readily disposable.

Another shortcoming that has not been overcome in the prior art designs is the provision of a single device that facilitates the intimate introduction of antimicrobial solution into and under the cuticle areas. While stiff bristles can penetrate the cuticle area and a sponge can supply antiseptic solution, no device has been described that efficiently fulfills both functions simultaneously.

SUMMARY OF THE INVENTION

It is an object of the present invention to provide a scrub sponge that can be used to effectively clean both the exposed surfaces of the arms and hands, as well as the more inaccessible areas in between the fingers and especially in and around the cuticles;

It is a further object of this invention that the whole device be substantially deformable so that the sponge can be maneuvered in rather restricted areas;

It is another object of the invention that the entire construction be of foam;

It is a further object of the invention to provide scrubbing surfaces on the sponge device;

It is another object of this invention for the sponge to retain an antiseptic solution;

It is another object of the invention to provide a readily accessible storage niche for a fingernail cleaner; and It is a further object that the sponge device be continuously storable in an antiseptic solution saturated condition ready for immediate use.

According to the present invention, the foregoing and other objects are attained by the scrub sponge of the present invention. The multicomponent all-foam construction of the scrub sponge of the present invention affords the advantages of being deformable to allow cleaning in between fingers, ability to retain the antiseptic solution with which it is impregnated, and simultaneously provide an effective scrubbing surface. The composition and shape of the sponge allows a firm grasp, while a reinforced serrated slit in its center permits insertion of a finger to facilitate cleaning and disinfecting of the cuticle area. The toothed surfaces of the sponge provide an augmented scrubbing capability. In addition, a niche is provided within the scrub sponge's interior which can accommodate a fingernail pick. The sponge is hermetically sealed within a foil package and is ready for immediate use.

BRIEF DESCRIPTION OF THE DRAWINGS

Other objects and many attendant advantages of this invention will be readily appreciated as the same becomes better understood by the reference to the following detailed description, while considered in conjunction with the accompanying drawings, in which like reference numerals designate like parts throughout the figures thereof, and wherein.

DETAILED DESCRIPTION OF THE PREFERRED EMBODIMENTS

Figure 1:
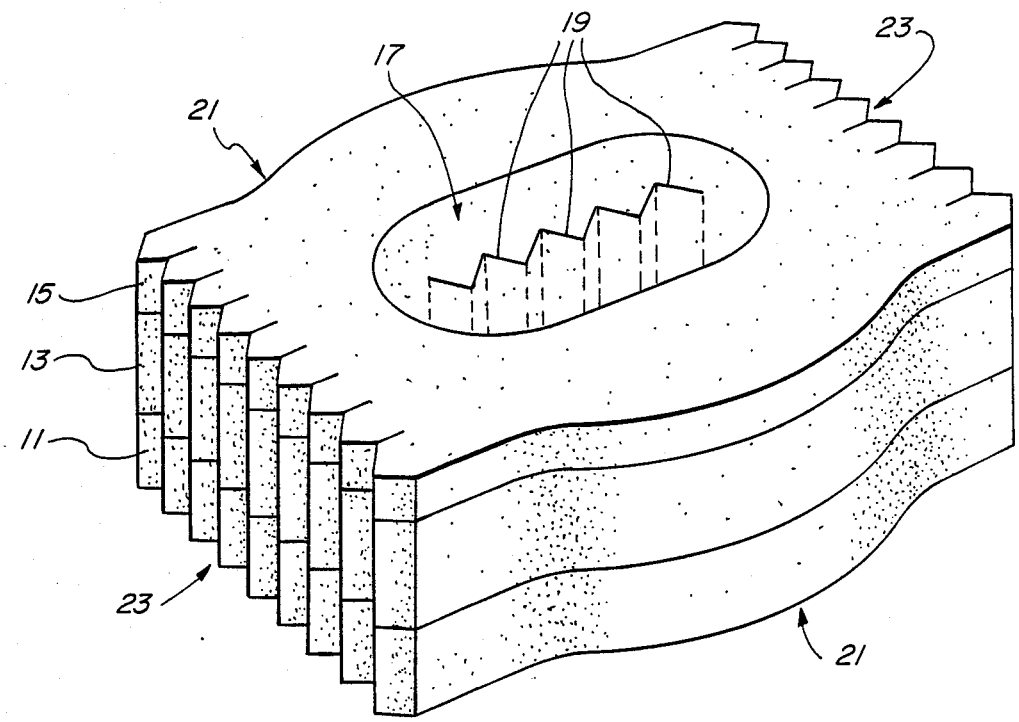
FIG. 1 is a perspective view of the surgical scrub sponge of the present invention.
Figure 2:
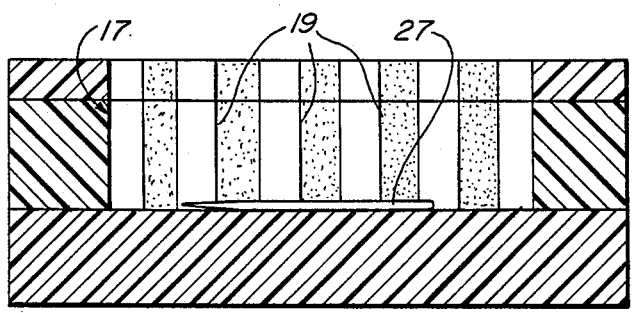
FIG. 2 is a cross-section of an embodiment of this invention.

FIG. 1 illustrates an embodiment of the present invention. The scrub sponge is made up of three layers of foam, a polyester foam layer 11, a polyether foam layer 13 and a thin polyethylene foam layer 15. A removable polyethylene foam insert 17 resides in the center of the structure and extends through the polyethylene foam and polyether foam layers. The insert has a serrated slit 19 running along its length and through its entire depth. Alternatively, the serration may be extended through the polyester foam layer. The scrub sponge is substantially rectangular in shape, having two slightly bulging sides 21 and two toothed sides 23. The trough between each tooth is extended 25 into the interior of the sponge. The sponge is impregnated with an antiseptic cleansing solution and a small fingernail pick 27 is positioned beneath the foam insert. The sponge is stored in its impregnated state within a sealed foil package (not shown) that may or may not be evacuated.

An important element of the present invention resides in the choice of materials, i.e., the use of three layers of different types of foam material is an essential requirement. A reticulated open-cell foam is used in the first layer 11. The rather open and coarse structure presents a relatively rough surface which is well suited for scrubbing. A ¼- to ⅜-inch layer of reticulated polyester foam, for example, can fulfill such a function. The exposed surface of layer 11 is the operative surface of the sponge with which the majority of skin area can be cleaned.

The intermediate layer requires a foam material having an inherent "wicking" property which is well suited for retaining fluids. A sponge according to the present invention is impregnated with an antiseptic cleansing solution. A ⅜- to ⅝-inch layer of polyester foam has adequate wicking characteristics, and, although the polyether foam also has an open-celled structure, the cells are much tighter than in the reticulated polyester, and therefore are more fluid-retentive. Fluids are easily drawn into and retained by this type of structure, and can only be expelled by a decrease in the volume, such as by a deformation and squeezing. The arrangement of the impregnated polyether foam in close proximity to the scrubbing surface causes the antiseptic solution to be automatically dispensed as the sponge is worked over the surface to be cleaned.

The top layer is to provide a somewhat rigid support for the entire sponge and a ⅜-inch thick layer of polyethylene foam is especially suited therefor. The inherent properties of this foam provide a semirigid backbone to the rest of the sponge. A layer of this polyethylene material ensures that the whole sponge retains its overall shape even after substantial deformation, and in addition provides a structure that can easily be grasped.

Figure 4:
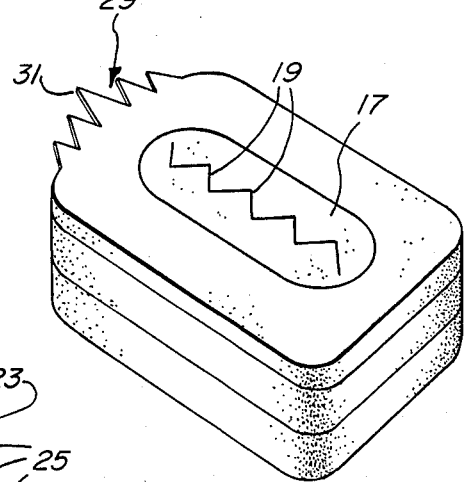
FIG. 4 is a perspective view of an embodiment of the invention.
Figure 3:
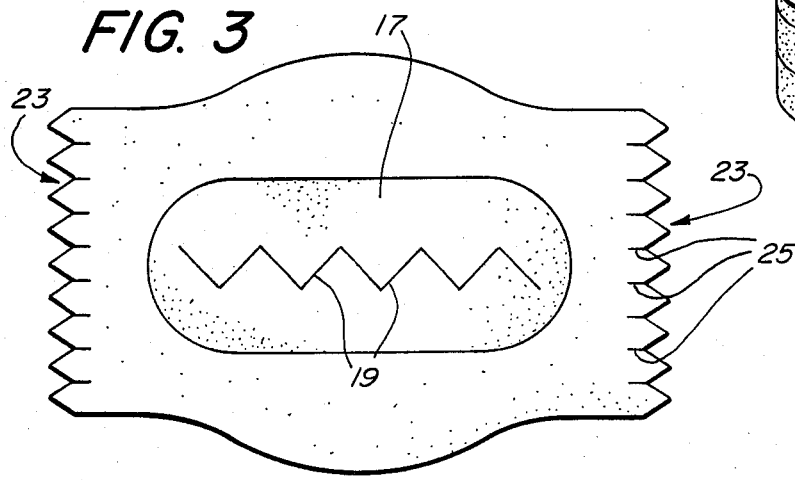
FIG. 3 is a top plan view of an embodiment of the present invention.

The insert 17 is made of the denser foam material and has a serrated slit 19 running longitudinally through its entire depth. The choice of material for the insert requires it to be sufficiently rigid to cause the cuticle areas to be distorted and pulled back as fingers are worked in and out of the slit and alternatively rotated therein. Tee serrated or zig-zagged shape of the slit augments the cleaning action when a finger is worked in and about the slit. A polyethylene foam similar to the top layer is a viable choice. Its location in the center of the sponge ensures an adequate supply of antiseptic cleansing solution, which readily flows through the polyethylene foam. The insert does not necessarily have to have an open cell structure, as its rigidity is the main concern and flow-through characteristics are less critical, as antiseptic solution can flow into the serrated slit from above or below as the sponge is distorted and flexed. Alternatively, the serration can be extended through the entire scrub sponge such that the fingers can be completely inserted into and through the entire sponge. The oblong configuration of the insert prevents its rotation within the sponge as fingers inserted therein are rotated. Since the insert is readily extractable, a fingernail pick 27 can be stored thereunder. Its location under the insert makes it quickly accessible, and its location in and within the antiseptic solution-soaked intermediate layer ensures that it is constantly bathed in the solution, such that when it is extracted and used, it has an ample supply of solution thereon. The fingernail pick can either be unattached and simply held in place by the presence of the insert or, alternatively, can be affixed to, for example, the bottom surface of the insert as illustrated in FIG. 4. The pick 29 comprises a thin section of polypropylene or nylon having a series of points 31 at one end with which the area below the fingernails can be cleaned. The pick 31 is glued directly onto the insert 17 and is removable and usable in conjunction with the insert. The projection of the points 31 beyond the edge of the insert aid in keeping the insert in place within the scrub sponge, where they extend into surrounding foam material. The pick is shaped so as not to interfere with a finger inserted entirely through the serrated slit.

The sandwich structure is formed by gluing the three layers together at their two interfaces using a hot melt type adhesive. Heating the adhesive material causes it to flow, at which point it is applied to the surfaces to be joined. The surfaces are subsequently joined, and upon cooling form an irreversibly fused sandwich. The sandwiched material is subsequently stamped or cut out into a desired configuration. An advantageous configuration is approximately four inches long, two to three inches wide, and approximately one to one and one-half inches thick. The edges along its long dimensions bulge outwardly in the middle. The bulged rectangular shape of the sponge falls easily to the human hand and ensures that upon gripping the sponge, a substantially rectangular shape remains. The edges of the sponge are cut in a toothed profile which presents a rougher surface and aids in the cleansing action. It has been found that the effectiveness of this profile is enhanced by extending the troughs between the teeth approximately an extra one-quarter inch 25 into the interior of the sponge. This presents the foam equivalent of a bristled surface.

The scrub sponge of the present invention is preferably dispensed in a sealed package such as a foil pouch. The surgeon or assistant simply extracts the sterile and impregnated sponge from its package and is ready to begin his cleanup. A vacuum packed configuration offers the additional advantage that the antiseptic solution would be forced deep into the sponge upon breaking of the seal. As the sponge is worked around the arms and hands, deformation of the structure causes the disinfectant solution to be squeezed out from the central layer and into the reticulated layer, where it is then worked into intimate contact with the areas being cleansed. The fact that the scrub sponge is wholly constructed of foam allows the scrub sponge to be temporarily deformed as necessary, such as when maneuvering the sponge in between the tight spots in between the fingers. The semirigid layer of polyethylene foam ensures that the sponge returns to its original shape, and, in addition, makes the sponge easier to grasp. The serrated slit centrally disposed in the sponge enables the insertion of fingers and is intended to facilitate the cleaning and disinfecting of the cuticle areas.

The use of the scrub sponge of the present invention constitutes a complete system, and no additional soaps or cleaning solutions or implements need be used. The scrub sponge, which comes in the sterile package, is used and then simply disposed of.

Obviously, many modifications and variations of the present invention are possible in light of the above teachings. It is therefore to be understood that, within the scope of the appended claims, the invention may be practiced otherwise than as specifically described.

What is claimed is:

1. A multi-component scrub sponge for use in cleansing arms, hands, fingernails and cuticles, comprising:

a first foam layer having a coarse and open-cell structure;

a second foam layer having a tight, semirigid distortion-resistant and fluid-retentive open-cell structure fused to the first foam layer, and;

a foam insert having a serrated slit therethrough, centrally and removably disposed in one of said first or second foam layers.

2. The scrub sponge of claim 1 wherein the insert is a semirigid distortion-resistant foam.

3. The scrub sponge of claim 2 wherein the insert comprises a polyethylene foam.

4. The scrub sponge of claim 1 further comprising a fingernail pick affixed to the insert on an interior surface.

5. The scrub sponge of claim 4 wherein the fingernail pick comprises a thin section of semirigid plastic having points protruding beyond all edges of the insert whereby the points can be used to clean under a fingernail and further serve to hold the insert in place within the scrub sponge by extending into surrounding foam material.

6. A multi-component scrub sponge for use in cleansing arms, hands, fingernails and cuticles, comprising:
a first foam layer having a coarse and open-cell structure; and
a second foam layer having a tight semirigid and fluid-retentive open-cell structure that resists distortion fused to the first foam layer;
said first and second foam layers being substantially rectangular with long sides and toothed short sides.

7. The scrub sponge of claim 6 wherein cuts in between the teeth extend into the sponge.

8. The scrub sponge of claim 7 wherein the first foam component comprises a reticulated polyester foam.

9. The scrub sponge of claim 8 wherein the second foam component is impregnated with an antiseptic/cleansing solution.

10. The scrub sponge of claim 9 further comprising a sealed pouch within which the scrub sponge including the impregnating antiseptic/cleansing solution is stored.

11. The scrub sponge of claim 7 wherein the second foam component comprises a polyether foam.

12. A three-layer foam scrub sponge, for use in cleaning arms, hands, fingernails and cuticles, having a contoured structure, comprising:
a first layer of coarse, reticulated foam;
a second layer of fluid-retentive foam fused to the first layer and impregnated with an antiseptic/cleansing solution;
a third layer of semirigid distortion-resistant foam fused to the second layer;
a foam insert having a serrated slit extending through its entire depth centrally disposed in the sponge so that the slit extends at least through the second and third layers, and
an overall contour substantially describing a rectangle with bulging long sides and toothed short sides.

13. The scrub sponge of claim 12 wherein the foam in between the teeth along the short sides is cut to a depth of approximately one-fourth inch.

14. The scrub sponge of claim 12 wherein the first layer comprises polyester foam.

15. The scrub sponge of claim 12 wherein the second layer comprises polyester foam.

16. The scrub sponge of claim 12 wherein the third layer comprises polyester foam.

17. The scrub sponge of claim 12 wherein the insert comprises polyester foam.

18. The scrub sponge of claim 12 further comprising a fingernail pick affixed to an interior surface of the insert.

19. The scrub sponge of claim 18 wherein the fingernail pick comprises a thin section of semirigid plastic having points protruding beyond all edges of the insert whereby the points can be used to clean under a fingernail and further serve to hold the insert in place within the scrub sponge by extending into surrounding foam material.

20. The scrub sponge of claim 12 further comprising a sealed pouch within which the impregnated sponge is stored and ready for use.

* * * * *